United States Patent
Kochura et al.

(10) Patent No.: US 10,892,057 B2
(45) Date of Patent: Jan. 12, 2021

(54) MEDICAL RISK FACTORS EVALUATION

(71) Applicant: International Business Machines Corporation, Armonk, NY (US)

(72) Inventors: Nadiya Kochura, Bolton, MA (US); Fang Lu, Billerica, MA (US)

(73) Assignee: International Business Machines Corporation, Armonk, NY (US)

( * ) Notice: Subject to any disclaimer, the term of this patent is extended or adjusted under 35 U.S.C. 154(b) by 0 days.

(21) Appl. No.: 15/287,364

(22) Filed: Oct. 6, 2016

(65) Prior Publication Data
US 2018/0101657 A1    Apr. 12, 2018

(51) Int. Cl.
| | |
|---|---|
| *G16H 50/30* | (2018.01) |
| *G16H 10/60* | (2018.01) |
| *G06N 20/00* | (2019.01) |
| *G16H 70/60* | (2018.01) |
| *G16H 50/70* | (2018.01) |
| *G16H 50/20* | (2018.01) |
| *G06F 19/00* | (2018.01) |

(52) U.S. Cl.
CPC ............ *G16H 50/30* (2018.01); *G06N 20/00* (2019.01); *G16H 10/60* (2018.01); *G16H 50/70* (2018.01); *G16H 70/60* (2018.01); *G06F 19/324* (2013.01); *G16H 50/20* (2018.01)

(58) Field of Classification Search
CPC ........ G16H 50/30; G16H 50/70; G16H 70/60; G16H 10/60; G16H 50/20; G06N 3/08; G06N 3/088; G06N 20/00; G06F 19/324
See application file for complete search history.

(56) References Cited

U.S. PATENT DOCUMENTS

| | | | |
|---|---|---|---|
| 7,433,856 B2 | 10/2008 | Wu et al. | |
| 7,899,764 B2 * | 3/2011 | Martin | G06Q 50/24 706/12 |
| 7,908,151 B2 | 3/2011 | Heckerman et al. | |
| 8,019,582 B2 | 9/2011 | Iliff | |
| 8,543,422 B2 | 9/2013 | Maman et al. | |
| 8,652,039 B2 | 2/2014 | Rosales et al. | |
| 2005/0032066 A1 | 2/2005 | Kiat et al. | |

(Continued)

FOREIGN PATENT DOCUMENTS

WO    2015023187 A1    2/2015

OTHER PUBLICATIONS

Kononenko, Machine learning for medical diagnosis: history, state of the art and perspective, Aug. 2001, Artificial Intelligence in Medicine, vol. 23, Issue 1, pp. 89-109. (Year: 2001).*

*Primary Examiner* — Christopher L Gilligan
(74) *Attorney, Agent, or Firm* — Jeffrey S LaBaw; Diana R Gerhardt

(57) ABSTRACT

A method, apparatus and computer program product for using a machine learning system to evaluate medical risks are described. A set of symptoms and a set of causal factors is used by the machine learning system to learn a set of association link formulas. Each of the association link formulas is used for calculating an association link strength between a respective symptom and a respective causal factor. An input set of symptoms for a first patient is received. The system determines which causal factors are relevant to the first patient according to association link strengths between respective ones of the relevant causal factors and the input set of symptoms. The set of relevant causal factors is sent for presentation to a user.

21 Claims, 10 Drawing Sheets

(56) References Cited

U.S. PATENT DOCUMENTS

| | | |
|---|---|---|
| 2007/0010718 A1 | 1/2007 | Spahn |
| 2008/0108881 A1* | 5/2008 | Stupp .................... G16H 50/20 600/300 |
| 2010/0070455 A1 | 3/2010 | Halperin et al. |
| 2012/0078837 A1 | 3/2012 | Bagchi |
| 2012/0084092 A1 | 4/2012 | Kozuch |
| 2012/0209625 A1 | 8/2012 | Armstrong |
| 2012/0253139 A1 | 10/2012 | Maman et al. |
| 2013/0282393 A1 | 10/2013 | Ebadollahi et al. |
| 2014/0046696 A1 | 2/2014 | Higgins |
| 2014/0279718 A1* | 9/2014 | Southey .................... G06N 5/04 706/11 |
| 2014/0279721 A1* | 9/2014 | Siegel ...................... G06N 5/02 706/11 |
| 2015/0193583 A1 | 7/2015 | McNair et al. |
| 2015/0242586 A1* | 8/2015 | Kagen .................... G06F 19/324 705/2 |
| 2015/0269347 A1 | 9/2015 | Bhatt et al. |
| 2015/0310163 A1* | 10/2015 | Kingsmore ............ G16B 20/00 506/38 |
| 2015/0310179 A1* | 10/2015 | Chengat .................. G06F 19/00 705/3 |
| 2016/0173690 A1* | 6/2016 | Perez ...................... G06F 17/16 379/265.03 |
| 2016/0292248 A1 | 10/2016 | Garcia |
| 2016/0379511 A1* | 12/2016 | Dawson ................ G06F 3/0482 434/362 |
| 2017/0011183 A1* | 1/2017 | Valverde, Jr. ......... G06F 40/169 |
| 2017/0124263 A1* | 5/2017 | Crafts, Jr. .............. G16H 40/20 |
| 2018/0068083 A1 | 3/2018 | Cohen |

* cited by examiner

MEDICAL RISK FACTORS EVALUATION

BACKGROUND OF THE INVENTION

This disclosure relates generally to machine learning. More particularly, it relates to teaching a machine learning system to recognize and present risk factors relevant to patient treatment.

To make an informative decision on the medical treatment of a patient, a doctor needs to gather data related to patient symptoms. In a manual process, a doctor will question a patient about their symptoms, recent history and consult the patient health record (PHR) data which the doctor may have available and evaluate this information based on the doctor's own experience in treating such symptoms. In many cases, the medical professionals follow the diagnostic protocols that match the patient symptoms to the average or typical patient profile for that set of symptoms, drug or treatment. One problem is that the information provided by these sources is limited, and the patient, for reasons which are not easily discovered by the doctor, may not fit an average patient profile. Causal factors for the symptoms may be missing from the record; these factors may be unusual such that they would not normally be discussed as part of a patient interview. Therefore, the doctor cannot make fully informed decision.

A number of computer aided mechanisms for improving the diagnosis of a patient have been proposed in the art. Further improvement in the computer aided mechanisms is needed.

BRIEF SUMMARY

According to this disclosure, a method, apparatus and computer program product for using a machine learning system to evaluate medical risks are described. A set of symptoms and a set of causal factors is used by the machine learning system to learn a set of association link formulas. Each of the association link formulas is used for calculating an association link strength between a respective symptom and a respective causal factor. An input set of symptoms for a first patient is received. The system determines which causal factors are relevant to the first patient according to association link strengths between respective ones of the relevant causal factors and the input set of symptoms. The set of relevant causal factors is sent for presentation to a user.

The foregoing has outlined some of the more pertinent features of the disclosed subject matter. These features should be construed to be merely illustrative. Many other beneficial results can be attained by applying the disclosed subject matter in a different manner or by modifying the invention as will be described.

BRIEF DESCRIPTION OF THE DRAWINGS

For a more complete understanding of the present invention and the advantages thereof, reference is now made to the following descriptions taken in conjunction with the accompanying drawings, in which.

DETAILED DESCRIPTION OF AN ILLUSTRATIVE EMBODIMENT

At a high level, in preferred embodiments of the invention, the present invention provides a set of causal factors for a set of input symptoms for patient diagnosis by a health care professional. A medical knowledge base is analyzed by a machine learning system to determine a set of association links representing the strength of relationships between respective causal factors and respective symptoms. Facts relating to patient experience and the causal factors are used to determine which of the causal factors are most relevant to the patient's symptoms. The medical knowledge base is dynamically updated by means of a plurality of data source plug-ins which update facts, causal factors and new health information. Thus, the most complete, up-to-date information about causal factors associated with the particular patient's symptoms is presented to the medical professional to aid in diagnosis and treatment recommendations.

Figure 1:
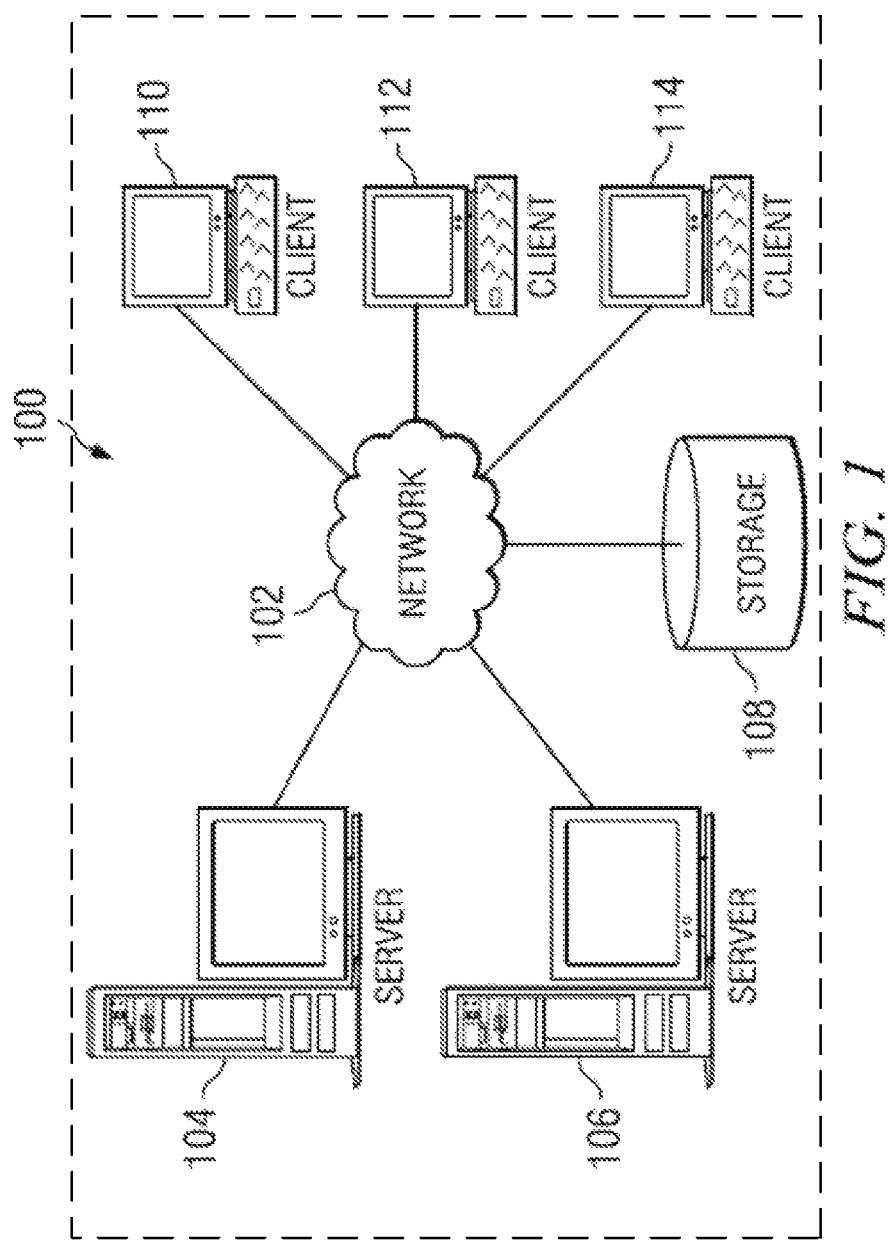
FIG. 1 depicts an exemplary block diagram of a distributed data processing environment in which exemplary aspects of the illustrative embodiments may be implemented.
Figure 2:
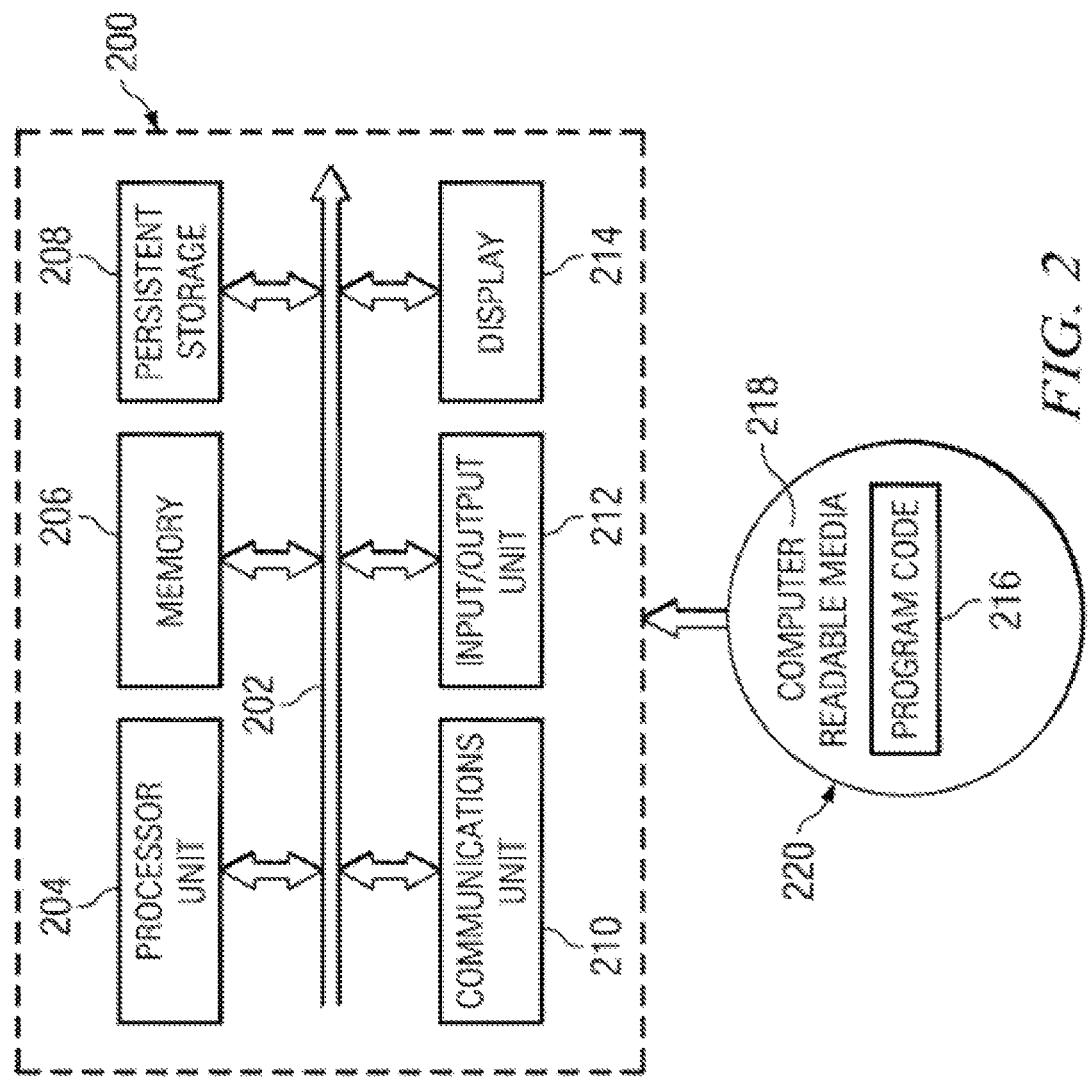
FIG. 2 is an exemplary block diagram of a data processing system in which exemplary aspects of the illustrative embodiments may be implemented.

With reference now to the drawings and in particular with reference to FIGS. 1-2, exemplary diagrams of data processing environments are provided in which illustrative embodiments of the disclosure may be implemented. It should be appreciated that FIGS. 1-2 are only exemplary and are not intended to assert or imply any limitation with regard to the environments in which aspects or embodiments of the disclosed subject matter may be implemented. Many modifications to the depicted environments may be made without departing from the spirit and scope of the present invention.

With reference now to the drawings, FIG. 1 depicts a pictorial representation of an exemplary distributed data processing system in which aspects of the illustrative embodiments may be implemented. Distributed data processing system 100 may include a network of computers in which aspects of the illustrative embodiments may be implemented. The distributed data processing system 100 contains at least one network 102, which is the medium used to provide communication links between various devices and computers connected together within distributed data processing system 100. The network 102 may include connections, such as wire, wireless communication links, or fiber optic cables.

In the depicted example, server 104 and server 106 are connected to network 102 along with storage unit 108. In addition, clients 110, 112, and 114 are also connected to network 102. These clients 110, 112, and 114 may be, for example, personal computers, network computers, or the like. In the depicted example, server 104 provides data, such as boot files, operating system images, and applications to the clients 110, 112, and 114. Clients 110, 112, and 114 are clients to server 104 in the depicted example. Distributed data processing system 100 may include additional servers, clients, and other devices not shown.

In the drawing, mainframe computer 116 is shown connected to network 102. Mainframe computer 116 can be, for example, an IBM System z mainframe running the IBM z/OS operating system. Connected to the mainframe 116 are mainframe storage unit 118 and client 120. Client 120 is either a PC connected directly to the mainframe communicating over a bus, or a console terminal connected directly to the mainframe via a display port.

In the depicted example, distributed data processing system 100 is the Internet with network 102 representing a worldwide collection of networks and gateways that use the Transmission Control Protocol/Internet Protocol (TCP/IP) suite of protocols to communicate with one another. At the heart of the Internet is a backbone of high-speed data communication lines between major nodes or host computers, consisting of thousands of commercial, governmental, educational and other computer systems that route data and messages. Of course, the distributed data processing system 100 may also be implemented to include a number of different types of networks, such as for example, an intranet, a local area network (LAN), a wide area network (WAN), or the like. As stated above, FIG. 1 is intended as an example, not as an architectural limitation for different embodiments of the disclosed subject matter, and therefore, the particular elements shown in FIG. 1 should not be considered limiting with regard to the environments in which the illustrative embodiments of the present invention may be implemented.

With reference now to FIG. 2, a block diagram of an exemplary data processing system is shown in which aspects of the illustrative embodiments may be implemented. Data processing system 200 is an example of a computer, such as client 110 in FIG. 1, in which computer usable code or instructions implementing the processes for illustrative embodiments of the disclosure may be located.

With reference now to FIG. 2, a block diagram of a data processing system is shown in which illustrative embodiments may be implemented. Data processing system 200 is an example of a computer, such as server 104 or client 110 in FIG. 1, in which computer-usable program code or instructions implementing the processes may be located for the illustrative embodiments. In this illustrative example, data processing system 200 includes communications fabric 202, which provides communications between processor unit 204, memory 206, persistent storage 208, communications unit 210, input/output (I/O) unit 212, and display 214.

Processor unit 204 serves to execute instructions for software that may be loaded into memory 206. Processor unit 204 may be a set of one or more processors or may be a multi-processor core, depending on the particular implementation. Further, processor unit 204 may be implemented using one or more heterogeneous processor systems in which a main processor is present with secondary processors on a single chip. As another illustrative example, processor unit 204 may be a symmetric multi-processor (SMP) system containing multiple processors of the same type.

Memory 206 and persistent storage 208 are examples of storage devices. A storage device is any piece of hardware that is capable of storing information either on a temporary basis and/or a permanent basis. Memory 206, in these examples, may be, for example, a random access memory or any other suitable volatile or non-volatile storage device. Persistent storage 208 may take various forms depending on the particular implementation. For example, persistent storage 208 may contain one or more components or devices. For example, persistent storage 208 may be a hard drive, a flash memory, a rewritable optical disk, a rewritable magnetic tape, or some combination of the above. The media used by persistent storage 208 also may be removable. For example, a removable hard drive may be used for persistent storage 208.

Communications unit 210, in these examples, provides for communications with other data processing systems or devices. In these examples, communications unit 210 is a network interface card. Communications unit 210 may provide communications through the use of either or both physical and wireless communications links.

Input/output unit 212 allows for input and output of data with other devices that may be connected to data processing system 200. For example, input/output unit 212 may provide a connection for user input through a keyboard and mouse. Further, input/output unit 212 may send output to a printer. Display 214 provides a mechanism to display information to a user.

Instructions for the operating system and applications or programs are located on persistent storage 208. These instructions may be loaded into memory 206 for execution by processor unit 204. The processes of the different embodiments may be performed by processor unit 204 using computer implemented instructions, which may be located in a memory, such as memory 206. These instructions are referred to as program code, computer-usable program code, or computer-readable program code that may be read and executed by a processor in processor unit 204. The program code in the different embodiments may be embodied on different physical or tangible computer-readable media, such as memory 206 or persistent storage 208.

Program code 216 is located in a functional form on computer-readable media 218 that is selectively removable and may be loaded onto or transferred to data processing system 200 for execution by processor unit 204. Program code 216 and computer-readable media 218 form computer program product 220 in these examples. In one example, computer-readable media 218 may be in a tangible form, such as, for example, an optical or magnetic disc that is inserted or placed into a drive or other device that is part of persistent storage 208 for transfer onto a storage device, such as a hard drive that is part of persistent storage 208. In a tangible form, computer-readable media 218 also may take the form of a persistent storage, such as a hard drive, a thumb drive, or a flash memory that is connected to data processing system 200. The tangible form of computer-readable media 218 is also referred to as computer-recordable storage media. In some instances, computer-recordable media 218 may not be removable.

Alternatively, program code 216 may be transferred to data processing system 200 from computer-readable media 218 through a communications link to communications unit 210 and/or through a connection to input/output unit 212. The communications link and/or the connection may be physical or wireless in the illustrative examples. The computer-readable media also may take the form of non-tangible media, such as communications links or wireless transmissions containing the program code. The different components illustrated for data processing system 200 are not meant to provide architectural limitations to the manner in which different embodiments may be implemented. The different illustrative embodiments may be implemented in a data processing system including components in addition to or in place of those illustrated for data processing system 200. Other components shown in FIG. 2 can be varied from the illustrative examples shown. As one example, a storage device in data processing system 200 is any hardware apparatus that may store data. Memory 206, persistent storage 208, and computer-readable media 218 are examples of storage devices in a tangible form.

In another example, a bus system may be used to implement communications fabric 202 and may be comprised of one or more buses, such as a system bus or an input/output bus. Of course, the bus system may be implemented using any suitable type of architecture that provides for a transfer of data between different components or devices attached to the bus system. Additionally, a communications unit may include one or more devices used to transmit and receive data, such as a modem or a network adapter. Further, a memory may be, for example, memory 206 or a cache such as found in an interface and memory controller hub that may be present in communications fabric 202.

Computer program code for carrying out operations of the present invention may be written in any combination of one or more programming languages, including an object-oriented programming language such as Java™, Smalltalk, C++, C#, Objective-C, or the like, and conventional procedural programming languages such as Python or C. The program code may execute entirely on the user's computer, partly on the user's computer, as a stand-alone software package, partly on the user's computer and partly on a remote computer, or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider).

Those of ordinary skill in the art will appreciate that the hardware in FIGS. 1-2 may vary depending on the implementation. Other internal hardware or peripheral devices, such as flash memory, equivalent non-volatile memory, or optical disk drives and the like, may be used in addition to or in place of the hardware depicted in FIGS. 1-2. Also, the processes of the illustrative embodiments may be applied to a multiprocessor data processing system, other than the SMP system mentioned previously, without departing from the spirit and scope of the disclosed subject matter.

As will be seen, the techniques described herein may operate in conjunction within the standard client-server paradigm such as illustrated in FIG. 1 in which client machines communicate with an Internet-accessible Web-based portal executing on a set of one or more machines. End users operate Internet-connectable devices (e.g., desktop computers, notebook computers, Internet-enabled mobile devices, or the like) that are capable of accessing and interacting with the portal. Typically, each client or server machine is a data processing system such as illustrated in FIG. 2 comprising hardware and software, and these entities communicate with one another over a network, such as the Internet, an intranet, an extranet, a private network, or any other communications medium or link. A data processing system typically includes one or more processors, an operating system, one or more applications, and one or more utilities.

Cloud computing is a model of service delivery for enabling convenient, on-demand network access to a shared pool of configurable computing resources (e.g. networks, network bandwidth, servers, processing, memory, storage, applications, virtual machines, and services) that can be rapidly provisioned and released with minimal management effort or interaction with a provider of the service. This cloud model may include at least five characteristics, at least three service models, and at least four deployment models, all as more particularly described and defined in "Draft NIST Working Definition of Cloud Computing" by Peter Mell and Tim Grance, dated Oct. 7, 2009.

In particular, the following are typical characteristics:

On-demand self-service: a cloud consumer can unilaterally provision computing capabilities, such as server time and network storage, as needed automatically without requiring human interaction with the service's provider.

Broad network access: capabilities are available over a network and accessed through standard mechanisms that promote use by heterogeneous thin or thick client platforms (e.g., mobile phones, laptops, and PDAs).

Resource pooling: the provider's computing resources are pooled to serve multiple consumers using a multi-tenant model, with different physical and virtual resources dynamically assigned and reassigned according to demand. There is a sense of location independence in that the consumer generally has no control or knowledge over the exact location of the provided resources but may be able to specify location at a higher level of abstraction (e.g., country, state, or datacenter).

Rapid elasticity: capabilities can be rapidly and elastically provisioned, in some cases automatically, to quickly scale out and rapidly released to quickly scale in. To the consumer, the capabilities available for provisioning often appear to be unlimited and can be purchased in any quantity at any time.

Measured service: cloud systems automatically control and optimize resource use by leveraging a metering capability at some level of abstraction appropriate to the type of service (e.g., storage, processing, bandwidth, and active user accounts). Resource usage can be monitored, controlled, and reported providing transparency for both the provider and consumer of the utilized service.

The Service Models typically are as follows:

Software as a Service (SaaS): the capability provided to the consumer is to use the provider's applications running on a cloud infrastructure. The applications are accessible from various client devices through a thin client interface such as a web browser (e.g., web-based e-mail). The consumer does not manage or control the underlying cloud infrastructure including network, servers, operating systems, storage, or even individual application capabilities, with the possible exception of limited user-specific application configuration settings.

Platform as a Service (PaaS): the capability provided to the consumer is to deploy onto the cloud infrastructure consumer-created or acquired applications created using programming languages and tools supported by the provider. The consumer does not manage or control the underlying cloud infrastructure including networks, servers, operating systems, or storage, but has control over the deployed applications and possibly application hosting environment configurations.

Infrastructure as a Service (IaaS): the capability provided to the consumer is to provision processing, storage, networks, and other fundamental computing resources where the consumer is able to deploy and run arbitrary software, which can include operating systems and applications. The consumer does not manage or control the underlying cloud infrastructure but has control over operating systems, storage, deployed applications, and possibly limited control of select networking components (e.g., host firewalls).

The Deployment Models typically are as follows:

Private cloud: the cloud infrastructure is operated solely for an organization. It may be managed by the organization or a third party and may exist on-premises or off-premises.

Community cloud: the cloud infrastructure is shared by several organizations and supports a specific community that has shared concerns (e.g., mission, security requirements, policy, and compliance considerations). It may be managed by the organizations or a third party and may exist on-premises or off-premises.

Public cloud: the cloud infrastructure is made available to the general public or a large industry group and is owned by an organization selling cloud services.

Hybrid cloud: the cloud infrastructure is a composition of two or more clouds (private, community, or public) that remain unique entities but are bound together by standardized or proprietary technology that enables data and application portability (e.g., cloud bursting for load-balancing between clouds).

A cloud computing environment is service-oriented with a focus on statelessness, low coupling, modularity, and semantic interoperability. At the heart of cloud computing is an infrastructure comprising a network of interconnected nodes. A representative cloud computing node is as illustrated in FIG. 2 above. In particular, in a cloud computing node there is a computer system/server, which is operational with numerous other general purpose or special purpose computing system environments or configurations. Examples of well-known computing systems, environments, and/or configurations that may be suitable for use with computer system/server include, but are not limited to, personal computer systems, server computer systems, thin clients, thick clients, hand-held or laptop devices, multiprocessor systems, microprocessor-based systems, set top boxes, programmable consumer electronics, network PCs, minicomputer systems, mainframe computer systems, and distributed cloud computing environments that include any of the above systems or devices, and the like. Computer system/server may be described in the general context of computer system-executable instructions, such as program modules, being executed by a computer system. Generally, program modules may include routines, programs, objects, components, logic, data structures, and so on that perform particular tasks or implement particular abstract data types. Computer system/server may be practiced in distributed cloud computing environments where tasks are performed by remote processing devices that are linked through a communications network. In a distributed cloud computing environment, program modules may be located in both local and remote computer system storage media including memory storage devices.

Figure 3:
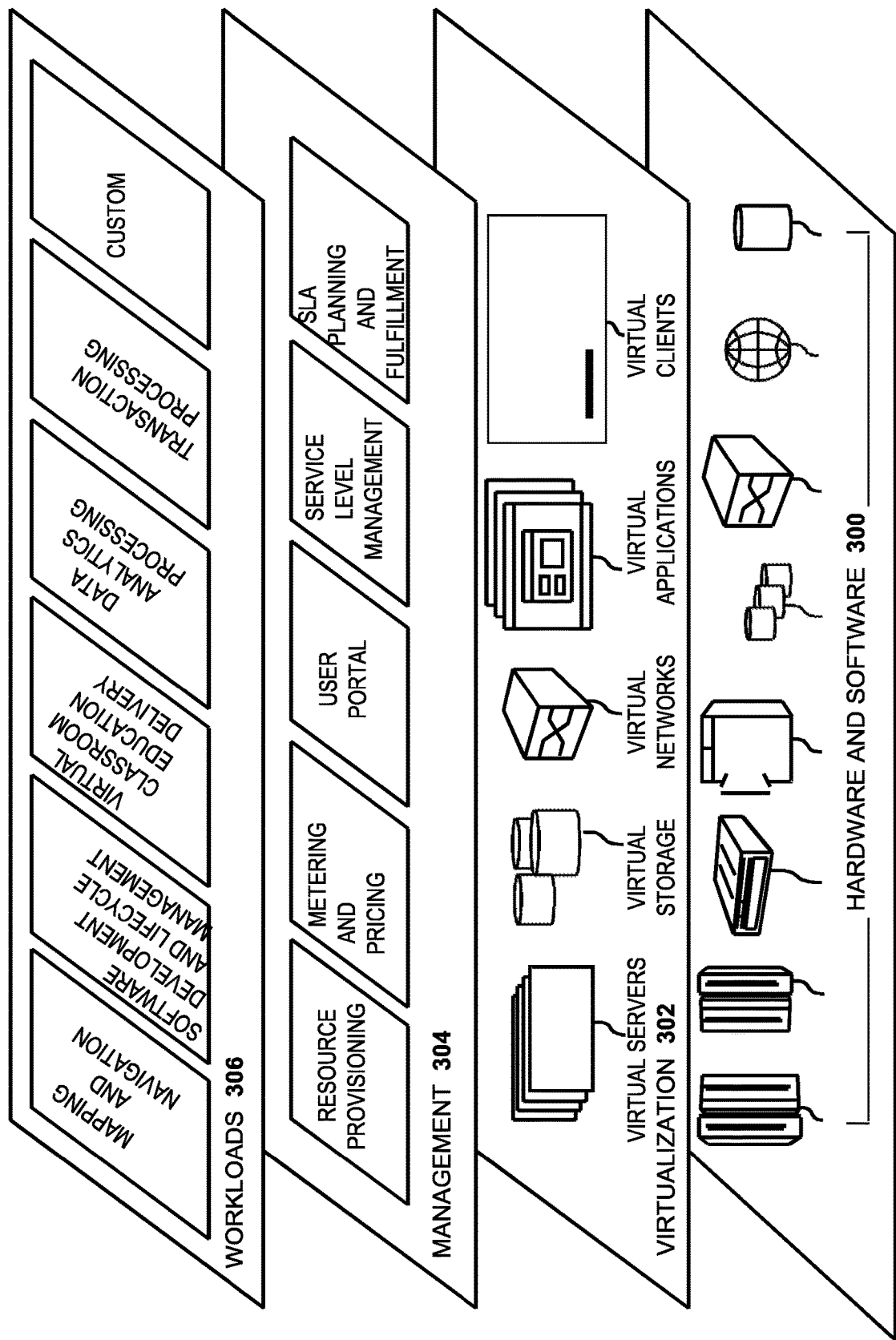
FIG. 3 illustrates an exemplary cloud computing architecture in which the disclosed subject matter may be implemented.

Referring now to FIG. 3, by way of additional background, a set of functional abstraction layers provided by a cloud computing environment is shown. It should be understood in advance that the components, layers, and functions shown in FIG. 3 are intended to be illustrative only and embodiments of the invention are not limited thereto. As depicted, the following layers and corresponding functions are provided:

Hardware and software layer 300 includes hardware and software components. Examples of hardware components include mainframes, in one example IBM® zSeries® systems; RISC (Reduced Instruction Set Computer) architecture based servers, in one example IBM pSeries® systems; IBM xSeries® systems; IBM BladeCenter® systems; storage devices; networks and networking components. Examples of software components include network application server software, in one example IBM WebSphere® application server software; and database software, in one example IBM DB2® database software. (IBM, zSeries, pSeries, xSeries, BladeCenter, WebSphere, and DB2 are trademarks of International Business Machines Corporation registered in many jurisdictions worldwide)

Virtualization layer 302 provides an abstraction layer from which the following examples of virtual entities may be provided: virtual servers; virtual storage; virtual networks, including virtual private networks; virtual applications and operating systems; and virtual clients.

In one example, management layer 304 may provide the functions described below. Resource provisioning provides dynamic procurement of computing resources and other resources that are utilized to perform tasks within the cloud computing environment. Metering and Pricing provide cost tracking as resources are utilized within the cloud computing environment, and billing or invoicing for consumption of these resources. In one example, these resources may comprise application software licenses. Security provides identity verification for cloud consumers and tasks, as well as protection for data and other resources. User portal provides access to the cloud computing environment for consumers and system administrators. Service level management provides cloud computing resource allocation and management such that required service levels are met. Service Level Agreement (SLA) planning and fulfillment provides pre-arrangement for, and procurement of, cloud computing resources for which a future requirement is anticipated in accordance with an SLA.

Workloads layer 306 provides examples of functionality for which the cloud computing environment may be utilized. Examples of workloads and functions which may be provided from this layer include: mapping and navigation; software development and lifecycle management; virtual classroom education delivery; data analytics processing; transaction processing; and others (e.g., enterprise-specific functions in a private cloud).

It is understood in advance that although this disclosure includes a detailed description on cloud computing, implementation of the teachings recited herein are not limited to a cloud computing environment. Rather, embodiments of the present invention are capable of being implemented in conjunction with any other type of computing environment now known or later developed.

To make an informative decision on medical treatment, a doctor needs to assess multiple causal factors related to the patient symptoms and match those against patient information such as patient interview data or patient health record (PHR) data. In many cases, the medical professionals follow the diagnostic protocols that match the patient symptoms to the average or typical patient or recipient for that drug or treatment.

There are at least two problems with the typical protocol. The doctor may be missing patient information which is important to identify the cause or causes of the patient symptoms. The doctor may be unaware of new advances in the treatment of a particular symptom or disease. Though particular patient symptoms and PHR data can be a "perfect match" to the average candidate patient for a given treatment, as symptoms are common to multiple diseases or conditions, it is possible that for the particular patient, there might be causal factors contributing to the symptoms that are not known to the doctor. Therefore, the doctor cannot make a fully informed decision.

However, although the information may not be available to the doctor either by interviewing the patient or in the PHR data, the information on a relevant causal factor may exist, unknown to the doctor or the patient. One of the problems is that information linking many of the causal factors may only exist as data that is scattered across various data sources; each data source requires its own access protocol, user knowledge of available data and search protocol. As it is difficult enough for the doctor to keep abreast of medical advances, keeping abreast of new data sources compounds the difficulty of gathering the needed information. Further, weighing which factors that can contribute or cause symptoms and are relevant to the particular patient is a difficult task. For example, the level of relevancy for a particular causal factor can be different for various symptoms or diseases. As mentioned above, the diagnosis protocol also needs to take into account advances in medical knowledge. In summary, the inventors have determined that to improve the doctor's decision making process and to reduce the risk of errors in treatment, a solution is required that provides additional relevant and supportive causal factor data, and preferably, new advances in medical knowledge. In preferred embodiments, the solution provides explanations as to how the additional causal data and new medical protocols are relevant to the patient and their symptoms.

The inventors disclose a solution that provides dynamic data related to patient symptoms which allows the doctors to be aware of relevant causal factors causing the symptoms as well as to filter out unnecessary or irrelevant factors and thereby provide the correct medical treatment. The solution improves the quality of the health services by reducing doctor errors, e.g., the misdiagnosis, overmedication, outdated treatment, and by providing more personalized medical care.

The inventors recognized that doctors and other health professionals have a great tendency to match a current patient to the average, or expected, profile based on a common set of symptoms. For example, the decision if the patient has a disease D which must be treated with prescription T is based on the pattern matching of the patient symptoms and PHR (patient health record) attributes with an average profile, which may or may not fit the current patient problems, if all the relevant causal factors were known. However, evaluating all relevant causal factors requires significant knowledge and information processing capabilities. Further, as is mentioned above, in many cases, the needed information is scattered across various data sources.

The goal of the solution is to provide a method that dynamically generates a set of additional attributes or causal factors that can be taken in consideration during the decision making process. The system generates association links between a set of symptoms and a set of relevant causal factors. In preferred embodiments of the invention, a set of the causal factors are environmental factors which may be determined by system access to non-medical types of data sources. In embodiments of the invention, association links are calculated by functions that define the degree to which a given causal factor, e.g., an environmental factor, is relevant to a given symptom. At some point the system receives and presents data identifying a patient's current symptom, e.g., a medical dashboard operated at a point of care by a medical professional. The system dynamically retrieves monitored data such as geographical, temporal and environmental facts which are in turn used to determine whether a particular causal factor is relevant to a particular patient's symptoms. In embodiments of the invention, facts are used to generate values for causal factors used in calculations for the association links. Also, facts can be used to determine which causal factors should be applied to the association links for the particular patient, linking factors to symptoms, and identifying which factor or set of factors is the most likely cause of the symptom. Given the set of relevant causal factors, an appropriate treatment plan can be recommended.

The dynamic use of "outside" data to augment the normally available "patient data" to evaluate likely causes of symptoms to identity a set of causal factors for the particular patient, beyond the typical causes associated with the symptoms for an average patient is believed novel. In particular, data from non-medical databases can be used to identify environmental causal factors. In preferred embodiments of the invention, the dynamically monitored data sources include predefined environmental factors to identify the likely cause of a symptom. In preferred embodiments of the invention, causal factors are grouped by category in a taxonomy, for example, factors can be organized into categories such as weather (pollution, moisture), social (Socio-economic status, crowding), nutrition (diet, food allergy) and genetic. The invention is particularly good at identifying "environmental factors" which occur outside the individual such as weather, exposure to pollution, pathogens or radiation, stress caused by social inequity. Other "internal factors" are considered as causal factors such as individual characteristics such as age, gender and genetic factors which might predispose an individual to a disease. Individuals can react differently to an environmental factor. As an example, an impurity in drinking water may trigger a symptom in one person's body, whereas the same chemical may have no effect at all in another person's body. In preferred embodiments of the invention, the system taxonomy of factors is pluggable, and built upon available medical sources. Thus, if new causal factors are extracted from new medical research, the taxonomy is easily updated. The system is open and flexible to additions or changes in the category hierarchy.

Figure 4:
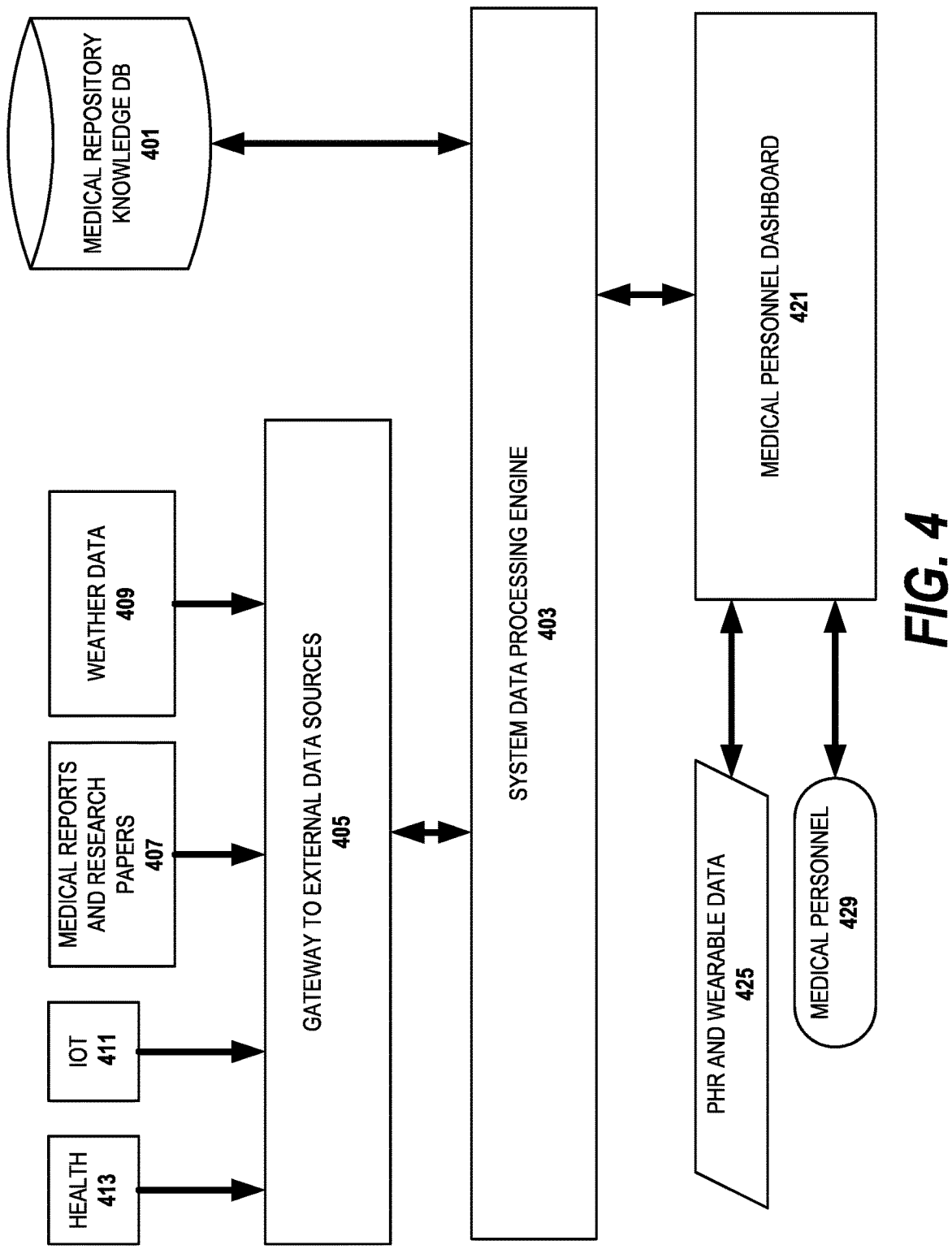
FIG. 4 illustrates a more detailed architectural diagram according to an embodiment of the invention.

FIG. 4 illustrates an architectural diagram according to a preferred embodiment of the invention. The system medical repository knowledge database (DB) 401 holds data needed to make decisions concerning causal factors relationships to symptoms. In preferred embodiments of the invention, the medical DB 401 is populated at the setup time with a compendium of medical knowledge and then is updated in real-time from trusted sources with relevant facts and medical protocols. In the set-up phase, the medical database 401 can be supplied with a curated set of data including causal factors, symptoms, diseases and treatments and their relationships. In a preferred embodiment, the database also includes textual evidence, e.g., excerpts from medical journals, which substantiate the relationships between the attributes stored in the database 401. In a second maintenance phase, the medical database 401 is updated at real time with new knowledge facts based on statistical data and research findings as well as information gathered from external data sources.

The system data processing engine 403 provides the interface between the medical repository knowledge DB 401 and the other elements of the system in this embodiment. The engine 403 retrieves new data from the gateway 405 to external data sources. This new information is normalized and provided to the medical repository database 401. In some embodiments of the invention, the engine 403 includes the algorithm(s) used to derive the relationships between the causal factors, symptoms, diseases and treatment. The gateway 405 is coupled to a plurality of plug-ins 407, 409, 411, 413 to external data sources which provide new data to the system. The external data sources are not depicted in the figure. Medical reports and research plug-in 407 provides new medical data and journal articles from trusted sources. Weather data is provided by weather plug-in 409 from sources such as government weather sources such as the US National Climatic Data Center or from private sources as the Weather Channel or the Weather Underground as well as from Internet of Things (IoT) devices which collect weather related information. Other IoT information can be collected by IoT plug-in 411 from IoT devices such as wearable devices and trackers. Wearable devices can collect external data such as weather related facts, i.e., temperature, humidity, location related facts and health related facts such as heat beat, sleep length and quality specific to the patient experience. That is, facts related to both environmental and internal causal factors can be collected by the wearable device. The collected patient health data provide extensions to the PHR data. A separate health plug-in 413 provides other medical information such as CDC alerts, reports from local hospitals, medical periodical statistical data. The gateway plug-ins 409-413 mentioned in this embodiment are exemplary, different plug-ins can be used in other embodiments to connect with trusted data sources for real time updates on the risk and causal factors. For example, multiple health plug-ins could be used in alternative embodiments, each plug-in dedicated to a specific health data feed.

The system data processing engine 403 also connects a medical personnel dashboard 421 to other system components. The dashboard 421 provides a graphical user interface for displaying information relevant to the patient symptoms. In particular, in preferred embodiments, it displays causal factors which have likely caused the patient symptoms and which are relevant for selecting among different treatment regimens. In this embodiment, the patient health record (PHR) and health related data from a wearable device 425 are shown local to the medical personnel 429 and the dashboard 421, e.g., information available in the doctor's office and retrieved directly by the medical personnel dashboard 421. In alternative embodiments, the PHR and wearable data is made available through a gateway plug-in and retrieved by the gateway 405, i.e. remote from the medical dashboard 421. The medical personnel 429 make queries through the interface of the dashboard 421. These queries will be handled by the system data processing engine (SDPE) 403 with subsequent queries to the medical repository DB 401 and/or gateway 405. For example, the doctor may enter the patient's symptoms including a cough symptom into the medical dashboard 421. The SDPE 403 will then query the medical repository DB 401 and/or gateway 405, resulting in a display of a possible causal factor, e.g., currently reported increased pollution in the patient home address area.

Figure 5:
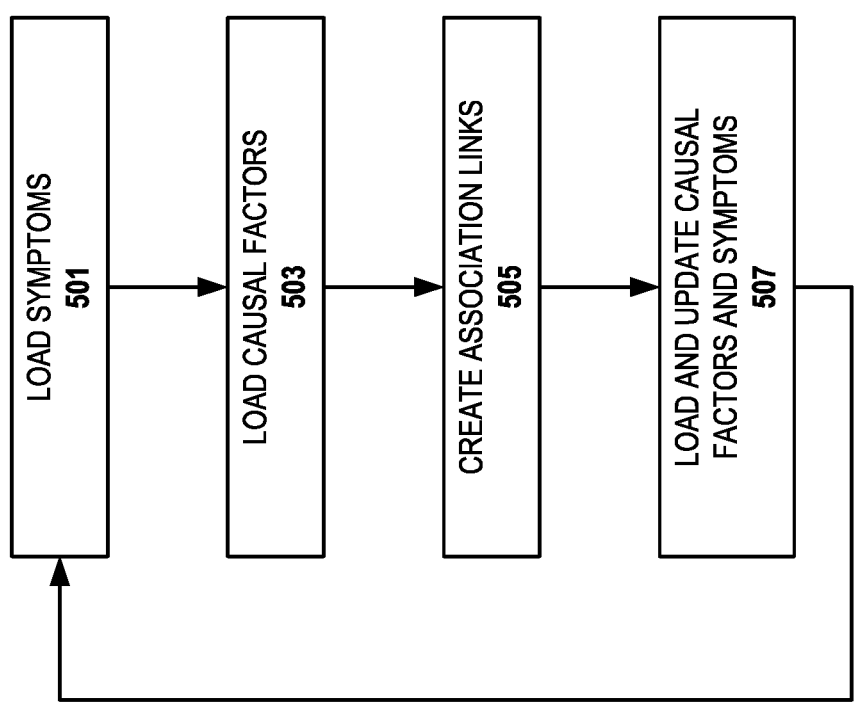
FIG. 5 illustrates a flow diagram of preparing the medical database according to an embodiment of the invention.

FIG. 5 illustrates a flow diagram of preparing the medical database according to an embodiment of the invention. In step 501, a set of symptoms is added to the system medical repository knowledge DB. The set of symptoms can be denoted as:

Symptoms SS={S1, S2, . . . }

In preferred embodiments of the invention, the symptoms are grouped by medical categories, for example, general symptoms, ocular symptoms, pulmonary symptoms and so forth.

In step 503, a set of causal factors are added to the system medical repository knowledge DB. The set of factors can be denoted as:

Factors=F: {f1, f2, . . . }

In preferred embodiments of the invention, the factors are grouped by categories, for example, environmental factors such as weather and social (e.g., poverty), food factors such as nutrition and allergy or genetic factors such as family background or genetically transmitted conditions, and so forth. Respective members of the set of causal factors are linked in a causal relationship to respective members of the set of symptoms. For example, weather factors are denoted as follows in embodiments in the invention:

F_weather={pollution, heat wave, high pressure air, wind, very cold, . . . }

Factors have properties that define values ranges. For example, pollution values={normal, extreme, low}

In alternative embodiments of the invention, similar data is added for diseases and treatments for those diseases.

In step 505, a set of association links are created. In preferred embodiments of the invention, the association links can be denoted:

Association Links=LS1_F1: {Ls1_f1, Ls1_f2 . . . }

Association links are entities that link symptoms to the factors, i.e. show the relationships between causal factors and symptoms. In preferred embodiments of the invention, the association links are created at the system setup time from processing medical sources and then are updated real time from the external sources coupled to the gateway. Association links have properties including a level of relevancy which defines how strongly or weakly a respective causal factor links to a respective symptom. Statistical methods are used to assess the strength of an association and to provide causal evidence. For example, the association link between the Symptom=cough and the Factor=pollution is stronger for people who have asthma.

In alternative embodiments of the invention, where similar data is added for diseases and treatments for those diseases, association links between symptoms and disease, and disease and treatments are calculated. In these embodiments, data about diseases and treatments is also stored in the medical repository knowledge DB. For example, at the system setup, the ontology of the diseases and categories is created based on the medical common categorization of the diseases. One such ontology is available in *International Statistical Classification of Diseases and Related Health Problems*, 10th Revision, Volume 2 Fifth edition, 2016 by World Health Organization. In those embodiments, where diseases and treatments are also used by the system, association links between a causal factor and a symptom for respective subgroups of the population can be calculated. For example, the association links for Symptom=cough and the Factor=pollution are likely to be stronger for people with asthma or lung disease than for the population at large.

In a simplified formula, the strength of an association link can expressed as:

Strength (L)=overall delta+sum {patient attributes*value} where overall_delta is the statistical value estimation of the link strength and sum{patient attributes*value} allows the system to adjust the statistical average with the patient concrete data. While a simple linear function is provided as an example, simplified formula, one skilled in the machine learning art will understand that when evaluating the value of the link or the strength of the association link, a variety of functions of greater complexity can be used. As the system processes the available data, in alternative embodiments, different algorithms may be evaluated sequentially to determine which is the "best fit" given the available data. As with use of machine learning algorithms, the exact mapping function used to calculate the strength of an association link is different based on the selection of the algorithm. Association links can be represented by some parametrized or weighted formula where parameters or weights of the facts are established or learned during the data processing or learning stage. The learned parameters or weights provide optimized values or the "best fit" for a given association link.

For example, the strength of an association link between the causal factor "pollution" to the symptom can be expressed as:

Link cough_pollution strength_Asthma=0.1+(0.2*1+ . . . ) for people with asthma, or,
Link cough_pollution strength_NoAsthma=0.1+ (0.2*0+ . . . ) for people without asthma.

This example shows that the factors' weights are learned during the learning phase of the machine learning algorithms. In this particular case, it shows that the impact of the pollution on people with asthma that have a cough is stronger than on people with a cough that have no asthma. The example also shows that the attribute value overall_delta is established or learned during the system learning stage. The overall_delta attribute allows the system to distinguish between the impacts of various factors linked to the same symptom regardless of the given patient data.

In step 507, the data about causal factors and symptoms are dynamically updated. In preferred embodiments of the invention, this is accomplished by new updates from the external data feeds from the gateway and plug-ins. In different embodiments of the invention, the updating is performed according to a polling interval or asynchronously as new data is transmitted by the external sources to the gateway. Another embodiment of the invention pulls data from the gateway plug-in in response to a new query from the medical personnel dashboard.

The system updates the formulas for calculating the set of association links based on the system configuration. The recalculation of the association link formulas can be done on demand or at each system upgrade cycle. Alternatively, the weights of the association link formulas are automatically calculated each time new relevant information is received from the gateway. In yet other embodiments, a decision is made in some embodiments as to whether the new information is sufficient to require that new association links should be calculated. For example, once a predetermined amount of relevant information for a particular association link, the system will recalculate the particular association link. An example of relevant information would be information about the particular causal factor or the particular symptom for which the association link is calculated. The threshold for the predetermined amount of information can change based on how much information relevant to the association link has already been used to calculate the association link.

In preferred embodiments of the invention, a "facts" database is kept within the overall medical repository knowledge database. In preferred embodiments of the invention, the facts database is populated at set-up time from a curated database. In addition, the facts database stores the real time updates to data related to causal factors received from the gateway plug-ins connected to the medical and external data sources.

Facts are related to the causal factors and defined with a set of properties. Facts are used to calculate values of the causal factors for respective individuals as well as for classes of individuals. In some cases, the value(s) of a fact may be the value of a causal factor for a particular patient at a particular time and location. In other cases, the facts are used to calculate the value of a causal factor for a particular patient at a particular time and location.

In some embodiments of the invention, the accuracy of the calculation of the association links for a given patient depends on whether all the required attributes and factors have available known values for the facts used in the association link calculation. As mentioned above, association links are entities that link, or show the relationship of, symptoms to the causal factors. If an association link algorithm includes the causal factors, but there are missing facts needed to find the value of the causal factors, then the association link cannot be evaluated properly. The doctor will be prompted for additional fact data and can request more data from the system to perform additional searches on the required facts or can ask the patient as part of the patient interview.

In preferred embodiments of the invention, facts are data entities that are expressed through the name-value pairs and provide content for the causal factors as is standard notation for the knowledge data bases. For example, facts for a weather causal factor can be expressed as: {fact1: name=pollution, value=large}, {fact2: name=wind, value=strong}

In alternative embodiments, the facts database could store the facts as a string or vector of categorized values. For example, a set of location based, weather related facts can be expressed as:

Facts_F_weather={fact1: {name-=pollution, location=$X$,value=large},fact2: {name=temp, location=$Y$,value=heat wave},fact3 . . . }

In embodiments of the invention, the facts database contains facts relating to the symptoms, diseases and treatments and which are used in calculating the association links between those attributes.

Figure 6:
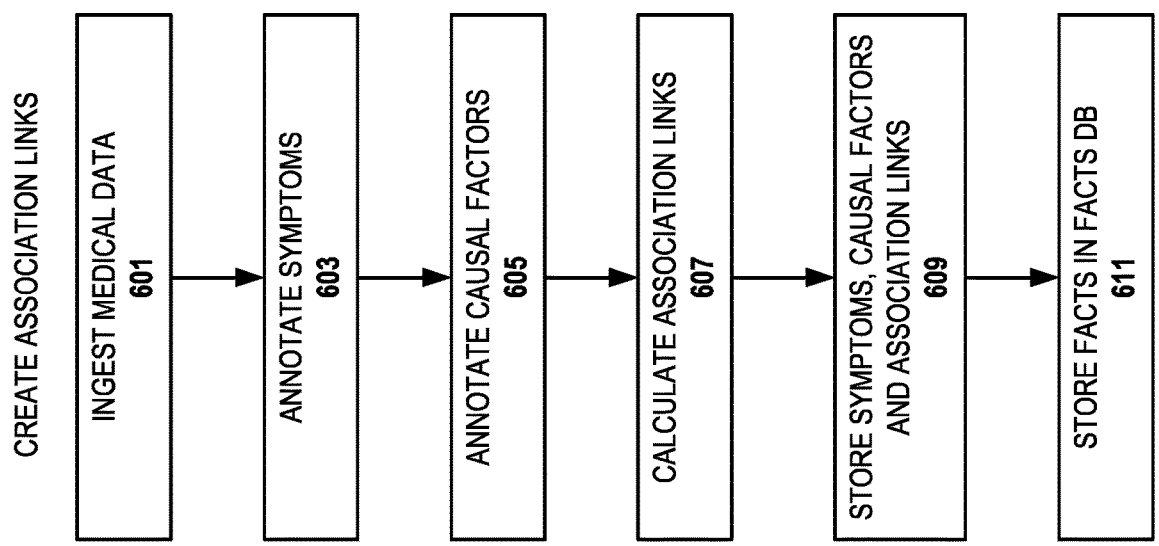
FIG. 6 illustrates a flow diagram of creating association links according to an embodiment of the invention.

FIG. 6 illustrates a flow diagram of creating association links according to an embodiment of the invention. In this embodiment, at least a portion of the causal factor, symptom, disease and treatment data is derived from a natural language analysis of medical reports and medical journal data. In step 601, the system begins to ingest the medical data. One known system of analyzing natural language unstructured and structured data is by using a set of annotators to identify and extract domain specific information. Annotators are well known in the field of machine learning and are frequently customized for specific domains of knowledge and repositories of data. Next in step 603, a symptom specific annotator will identify and extract symptom specific information found in structured or unstructured medical records. The causal factors annotator will identify and extract causal factors information in step 605. In preferred embodiments of the invention, the relationships between the identified symptom and causal factor data will be calculated as association links in step 607. This process is discussed in greater detail below. In some preferred embodiments, the relationship of the causal factors and the symptoms, either semantically "Symptom X is caused by factor Y" or by proximity of the respective symptom and causal factor in the medical record can be used as data to establish the existence of an association link. In step 609, the symptoms, causal links and the calculated associated links are stored in the medical knowledge repository. Finally, in some embodiments, facts are annotated and extracted from the annotated medical records and stored in the facts database of the medical knowledge repository as depicted by step 611. The step of annotating and storing facts can occur before the calculation of the association links, if the embodiment of the invention uses the facts to calculate the association links.

In preferred embodiments of the invention, standard machine learning algorithms are applied to statistically learn the weights in the association link algorithms. Some examples of suitable machine learning for embodiments of the invention are supervised machine learning algorithms such as support vector machine (SVM), neural network learning or decision tree machine learning algorithms.

In alternative embodiments of the invention where association links between disease, treatment and the symptoms are calculated, additional steps annotating and extracting information about these parameters are part of the process.

Figure 7:
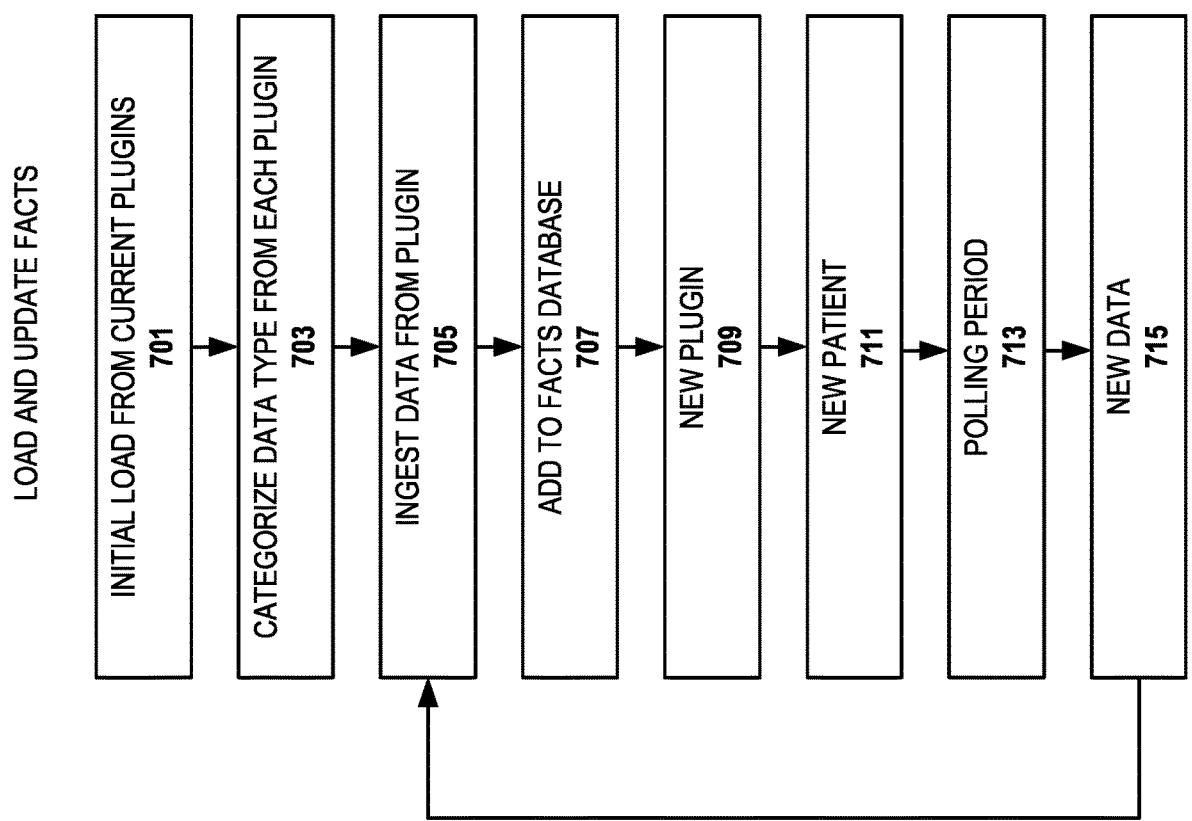
FIG. 7 illustrates a flow diagram of loading and updating facts according to an embodiment of the invention.

FIG. 7 illustrates a flow diagram of loading and updating facts according to an embodiment of the invention. In step 701, the initial load from the current plug-in(s) is retrieved. This step might occur at the initial set-up of the medical knowledge repository, or at a set polling period wherein a set of plug-ins are queried for new data. Next in step 703, the data type(s) retrieved from each plug-in is categorized. For example, some external data sources will provide primarily weather or health data, but may also contain location based data which can prove useful to identify the relevant causal factors for a given patient. The data is ingested from each respective plug-in in step 705. A process such as that described above in reference to FIG. 6 can be used. Specialized annotators can be used for data from each plug-in, chosen according to the expected data types provided by the plug-in. Alternatively, when the plug-in data comes in a specific format, a specialized annotator for the plug-in is used in some embodiments. The extracted facts are added to the facts database in step 707.

As mentioned above in preferred embodiments of the invention, data is dynamically added to the medical knowledge repository and the facts database. This can be accomplished in several ways. As shown by step 709, when a new plug-in is added to the system, the initial load of available data from that plug-in is added to an already running system. If needed, or according to system configuration, based on the newly retrieved data on symptoms and causal factors, new association links are calculated, either for existing symptoms and causal factors which are already in the medical knowledge repository database, or for new symptoms and causal factors from the new plug-in, e.g., in the case that the plug-in is a medical health plug-in.

In step 711, a new patient can cause new queries to the set of plug-ins for data relevant to the new patient. Other events such as adding new doctors, new medical institutions, and hence an expanded service area, or a medical emergency can cause new queries to the plug-ins which will add data to the facts database and the medical knowledge repository. Step 713 illustrates that there is a predetermined polling period used in some embodiments of the invention. In response to the new data, step 715, the process returns to the ingestion step 705 to add to the facts database.

Figure 8:
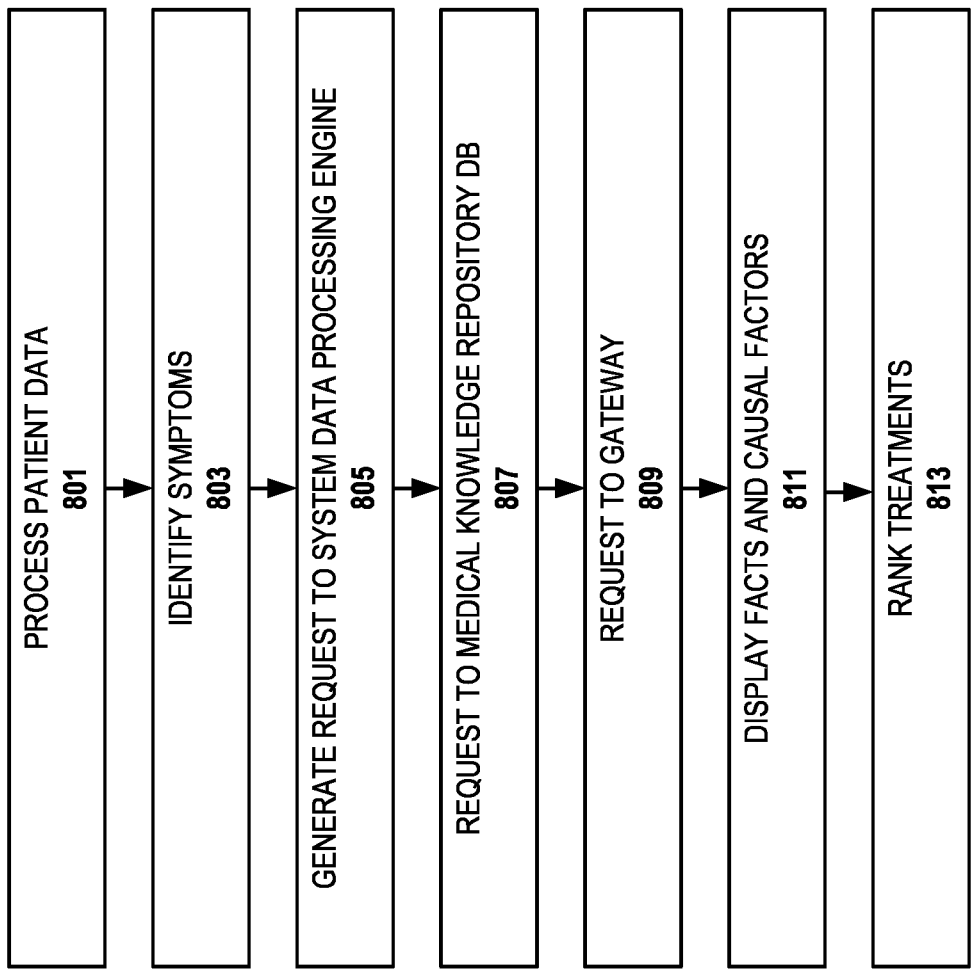
FIG. 8 illustrates a flow diagram of recommending a treatment according to symptoms according to another embodiment of the invention.

FIG. 8 illustrates a flow diagram of recommending a treatment according to symptoms according to another embodiment of the invention. In step 801, the patient data is processed for the current "visit". In embodiments of the invention, in a traditional patient visit to a health care professional equipped with the medical dashboard, the health care professional will retrieve the patient information locally available such as the patient health record (PHR) and any data from patient devices such as wearable devices or smartphones. In other embodiments, some patient data is available remotely. For example, the patient may be visiting a new doctor and the system processing engine makes queries to the system of the previous doctor for the PHR. In alternative embodiments, the patient visit may be a remote visit carried out via teleconference or video conference with the doctor; most of the patient information would be remote in this case.

Next in step 803, the patient symptoms are identified. Initially, this process includes a patient interview, doctor examination and manual entry of the symptoms into the medical dashboard. As discussed below, the process may be iterative as causal factors and patient facts are identified by the system. Once the symptoms are identified, the medical dashboard generates a request to the system data processing system in step 805 using the identified symptoms and patient data. In preferred embodiments of the invention, in step 807, the system data processing system generates a request to the medical knowledge repository database for the symptom, causal factor and association link data. This request can include a request to the facts database for facts which are relevant to calculating the association links for the particular patient. The request to the facts database is likely to be made subsequent to retrieving the symptom, causal factor and association link data so that the relevant facts for the patient are known.

The relevant facts are used in embodiments of the invention to not only calculate the value of an association link for a particular patient, but also to select among the algorithms used for calculating the association links, e.g., if the patient falls in a patient subgroup for which a special association link formula has been calculated. For example, if it is known in the PHR that the patient has asthma and a special set of association link formulas have been prepared in previous steps for asthma patients, those formulas will be used to calculate the strength of the association links.

In step 809, a request is optionally made to the gateway and plug-ins for additional patient data which is relevant to calculating the association links for the patient. This step could be taken if the patient data which is part of the request and or the medical knowledge repository lacks the information to calculate the association link weights. For example, suppose that the symptom, causal factor and association link data indicate that for a "cough" symptom, "pollution" as a causal factor is sometimes implicated, however, the patient data does not mention whether the patient lives in or has experienced a high pollution area. The system data processing engine creates a request to the plug-ins whether the patient address, previous patient addresses or locations in a patient travel itinerary are high pollution areas. As another example, if some patient symptoms indicate a particular disease, a query to the plug-ins will inquire whether the indicated disease was present in the areas that the patient has travelled or resided. Once assembled and calculated, the facts, association links and causal factors relevant to the input symptoms are displayed on the medical dashboard, as depicted by step 811. Preferably, the causal factors are displayed ranked in order of the association link strength. In embodiments of the invention, the medical professional will be prompted to enter candidate "missing" facts or symptoms or to verify whether the identified causal factors have actually been encountered by the patient. In some embodiments, facts or causal factors which the patient would not normally be aware of will not be presented in the prompt and instead the system will automatically make additional queries to the plug-ins for the missing facts.

In step 813, optionally, the treatments for the input symptoms are ranked and presented in the user interface of the medical dashboard. In embodiments of the invention in which prompting to enter missing facts or symptoms occurs, the ranking of the causal factors and treatments occurs before and after the correction and entry of missing facts. In cases where the ranking occurs before the correction, the medical professional can see the result of entering the additional or corrected data on the strength of the association links for different causal factors and the recommended treatment. In preferred embodiments of the invention, the strength of the association links between respective treatments with the strongest association links between the leading causal factors and entered symptoms is used in the ranking step.

In preferred embodiments of the invention, all relevant, retrieved information is provided to the doctor to help to make an informed decision. If any facts of relevant causal factors are not available in the system, the doctor can specifically request them, either by further patient interview or from additional queries to the system. The importance of respective facts to the patient diagnosis can be deduced from the association links. In preferred embodiments, the medical dashboard presents the facts, either as important facts or missing facts to the doctor, e.g., in the form of a ranking or different presentation manner, e.g., highlighting.

Figure 9:
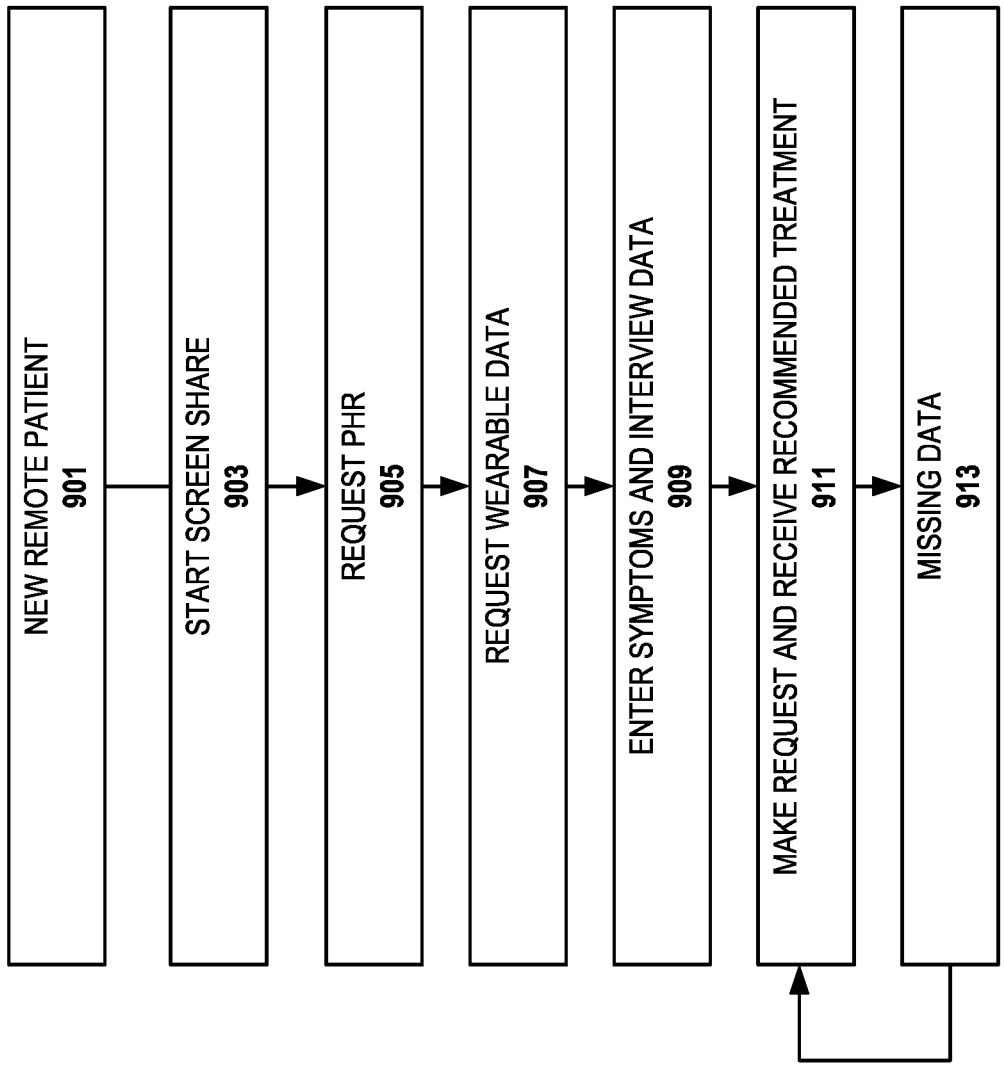
FIG. 9 is a flow diagram of collecting patient data and interacting with a medical dashboard according to another embodiment of the invention.

FIG. 9 is a flow diagram of collecting patient data and interacting with a medical dashboard according to another embodiment of the invention. The embodiment illustrated in the drawing portrays the steps taken within a doctor interaction with the system for a remote patient "visit". In step 901, a session is created with the remote patient. For example, many personal computers are equipped with a web camera allowing a session in which the doctor and patient interact. Optionally, in step 903, the medical professional starts a screen sharing session, e.g., a web conference, so that the patient can see the medical dashboard. Next, in step 905, the patient health record is entered, either by the patient or by a query from the medical dashboard to a local medical digital record system, e.g., if the patient is a current patient of the medical practice.

The patient's wearable data is requested in step 907. Personal computers, wearable devices and portable devices such as smartphones are commonly equipped with Bluetooth, or similar technology, so that the wearable data can be transferred to the patient's personal computer and then to the medical dashboard. In preferred embodiments of the invention, in step 909, the medical professional will continue to interview the patient and insofar as possible examine the patient for symptoms. The symptom and interview data is entered into the medical dashboard. In step 911, the medical dashboard will make a request to the system data processing engine for patient evaluation and receives a report from the system including data such as causal factors, facts and treatment recommendations. As discussed above, in some embodiments of the invention, the medical professional will be prompted by the medical dashboard to enter candidate "missing" data or to verify patient data, step 913. The figure illustrates an iterative process in which the treatments for the input symptoms are repeatedly ranked and presented in the user interface of the medical dashboard. If the session is shared with the patient, the patient can gain a better understanding for the process given different inputs.

A simplified example of how the system could be used by three patients having the same symptom, but after analysis, are given different recommended treatments is as follows. Given the notations:

D=disease, S=symptom(s), Ps=patient with symptom S, Fs=factors relevant to symptom S, Ff=facts relevant to causal factor F The system input includes:

The PHR personal health records for patients Ps1, Ps2 and Ps3.

The plug-in data from person wearables and trackers as extensions to the PHR.

The symptom S

The system task is, given a search space defined by the dominant symptom S, to establish optimized set of causal factors F_opt that need to be considered in a process of evaluating each of the patients Ps1, Ps2 and Ps3 to determine whether any of the patients with symptom S has a disease D that would require a treatment T. The system analyzes the causal factors relevant to the symptom S and populates causal factor values in vector F={fs1, fs2, . . . fsm} that has the relevant factors to the symptoms matching each of the patient Ps medical and external fact data. The system fetches the facts, Ff, relevant to the identified causal factors. In some embodiments of the invention, the retrieved facts are used to calculate the association link for the particular patient. The doctor is presented with the set of causal factors and corresponding facts in the process of the diagnosis protocol. If not all facts' values are known, the doctor can ask questions, perform additional research/clinical tests or make further queries to additional plug-in data sources.

Continuing the example:

S=cough

Fs={demographic, smoking, have family history of disease D, environment related factors (live on in the polluted air area) . . . }

There are 3 patients, Ps1, Ps2 and Ps3 identified with symptom S=cough.

For patient Ps1:

Ps1={ age=50, sex=male, smoking=occasional}, additional attributes={ allergy to mold=yes}, additional causal factors={lives in the highly humid area}

For patient Ps2:

Ps2={{age=50, sex=male, smoking=occasional}, additional causal factors={work outside as a constructor worker, exposed to increased pollution }}

For patient Ps3:

Ps3={{age=50, sex=male, smoking=occasional}, additional causal factors={came from region known with epidemic D and was not immunized for that disease}}

Based on additional factors analyzed, patient Ps1. was diagnosed as suffering from a mold allergy and was prescribed to install a dehumidifier at the house. Patient Ps2 was diagnosed as having a cough due to particulates and was prescribed to wear a mask while working. Patient Ps3 had a causal factor indicating exposure to epidemic D and was assigned to do additional clinical tests to acquire facts indicating whether it was the correct causal factor.

Figure 10:
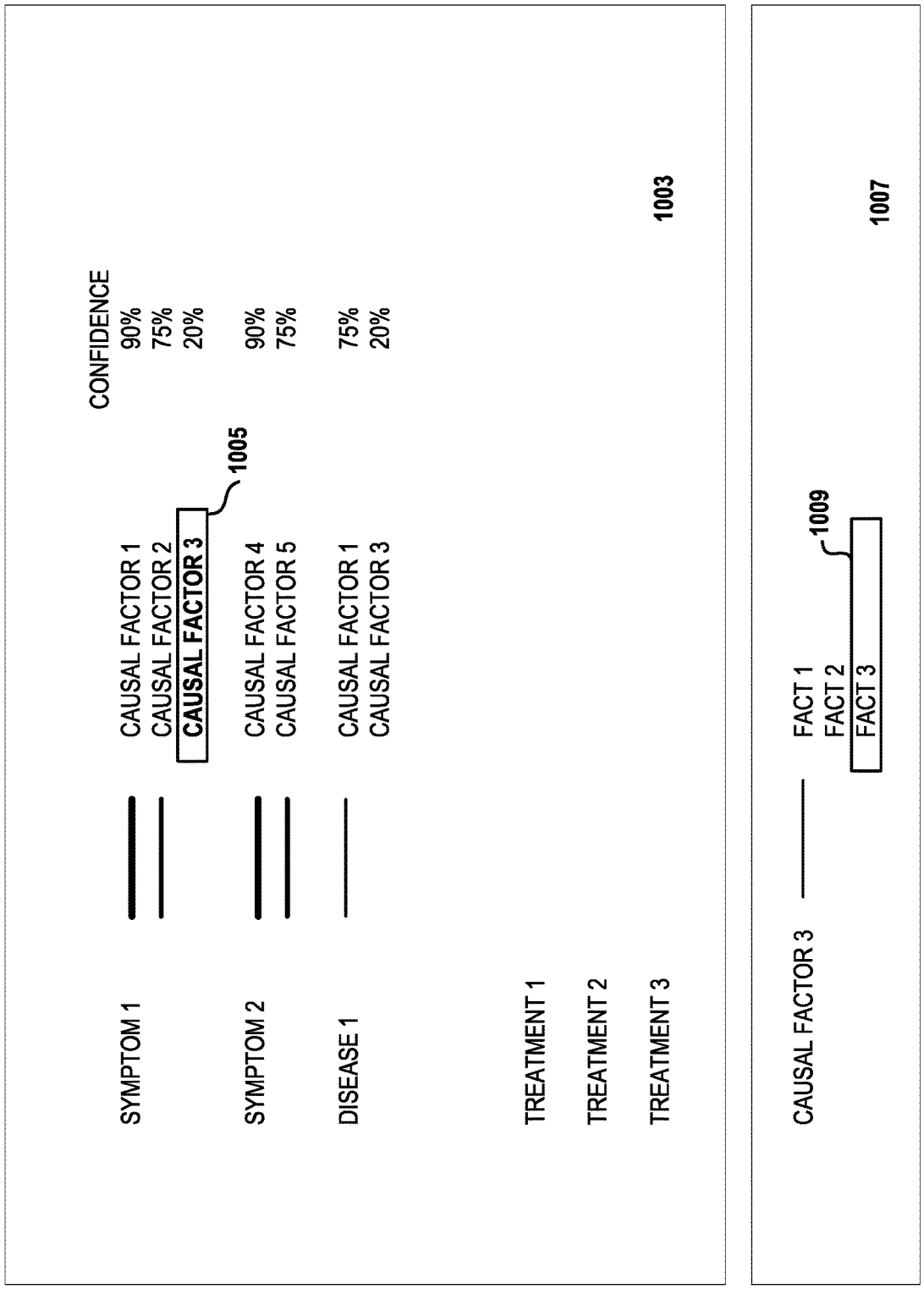
FIG. 10 is a diagram of a dashboard user interface of another embodiment of the invention.

FIG. 10 is a diagram of a dashboard user interface of an embodiment of the invention. The dashboard interface will have a view (not pictured) for entry of the patient symptoms. For example, the patient symptoms can be entered by keyboard entry, selection from a list of symptoms or voice recognition. Sending the set of symptoms to the system data processing engine as part of query will result in a response containing a set of causal factors back to the dashboard. Other views in the interface will include, but are not limited to, the patient health record (PHR) and health related data from a wearable device and other medical information related to the patient available in the doctor's office.

As illustrated in FIG. 10, the interface shows a view after the patient symptoms have been entered and the set of causal factors returned by the system in pane 1003. In the pane 1003, a "confidence level" is shown after each of the causal factors representing the strength of the association link between the respective symptom and causal factor. In the interface, the causal factors can be listed in order of relevance or more relevant factors can be displayed in a highlighted or otherwise distinctive manner as compared to other factors. Also illustrated in pane 1003, is a diagnosis of a set of most likely diseases in view of the symptoms and a set of causal factors which are most strongly related to the disease according to the medical knowledge base. Although not depicted, in alternative embodiments, a confidence level is displayed representing the strength of the association link between the disease and respective causal factor. A list of treatments for the set of symptoms or disease is also presented in pane 1003. This treatment list may be in order of preference based on the confidence level of causal factors, or according to selection of a candidate disease.

Greater detail is displayed in secondary pane 1007 if an element 1005 is selected in pane 1003. As shown in the figure, "causal factor 3" 1005 is selected by the medical professional. In this example, the selection results in a set of facts relevant to the patient which make the causal factor 3 relevant to the symptom, and hence to the diagnosis of the disease. In this example, the doctor selects the causal factor because of its low confidence level, thinking that the low confidence level may be due to missing facts. In embodiments of the invention, missing facts for a causal factor may be indicated by the manner in which the causal factor or confidence level is displayed, e.g., by a color or highlight. The doctor may be prompted by the interface for missing facts in other ways.

In FIG. 10, a particular fact, shown as FACT 3 1009 in the interface, can be displayed in a unique manner indicating that the fact is missing from the information assembled by the system. In such a case, the medical professional is thus prompted to interview the patient for the missing information or to ask the system to conduct further queries from the plug-ins for the missing fact. If the missing fact is found, confirmed and entered in the system, the display may change. For example, the confidence level may increase or the causal factor may be further highlighted.

The selection of the confidence level in preferred embodiments of the invention results in a display of the evidence, e.g., medical journal articles, which indicate why the system is confident about the association between the causal factor and the symptom. The selection of the confidence level may also result in a display of facts such as a excerpt from a patient health record (PHR) or data from a wearable device which supports the confidence level.

In preferred embodiments, more than one disease can be presented and selected by the medical professional. In these preferred embodiments of the invention, it is important that medical professional do the actual diagnosis, based on the best information possible. Selection of a disease can change the display of data in information pane 1003, showing different causal factors, confidence levels and suggested treatments. By switching between two displays of different diseases, it would be easy for the medical professional to see which diagnosis the system is more confident in, the supporting evidence and facts and which information may be missing for a proper diagnosis.

A few examples of how embodiments of the invention are used follows.

There is a body of medical research which shows that those who live near roads face a particularly high risk of heart disease, including sudden cardiac death, cancer and respiratory conditions, such as COPD and that these diseases are associated with air pollution. When such medical journals are ingested by the system, the causal factors, symptoms and diseases are annotated and entered in to the medical knowledge base. When a doctor encounters a patient with symptoms matching one of these diseases, i.e. heart disease, and selects a confidence level for patient location as a causal factor, evidence such as "According to a new study from the American Heart Association, healthcare providers should consider more carefully the impacts of air pollution. "On a population level, living near a major roadway was as important a risk factor [for cardiac death] as smoking, diet or obesity," Jaime E. Hart, Sc.D., study lead author and an instructor in medicine at Brigham and Women's Hospital and Harvard Medical School in Boston, Massachusetts" can be displayed in the user interface of the medical dashboard. When the symptom is identified with increased air pollution, the system associates the patient work/home location to establish the relevancy of the causal factor to the patient symptom data and provides "pollution" as one of the relevant causal factors to the doctor.

As another example, wildfires also cause respiratory health issues for residents. Yet a patient may not be aware of the effect of a wildfire and a remotely located doctor may not think to include a question about wildfires in the patient interview. Nonetheless, in embodiments of the invention, the system can associate the patient location by mapping the patient home and work locations with the location and timing of wildfires from a weather plug-in, establish an association link to the patient symptoms data and provide the additional wildfire causal factors to the doctor. In this example, the patient has a respiratory problems and since the smoke is a causal factor for respiratory problems, the system determines that the patient home was in a smoke area recently. The system provides this relevant information to the doctor for consideration in the diagnosis/treatment.

As yet another example, the system may be configured to pull the environment and weather information matching a patient's home and work addresses over time. For example, the home and work addresses are available from the PHR, and the environment and weather information are available from the plug-ins (if not already stored in the medical knowledge base). Thus, the causal factor and related facts data can be updated dynamically by the system. For a thorough diagnosis, this data needs to be considered in the context of the symptom and within the particular time frame where the patient was working and living. Say, there was a construction or industrial accident in the year 2015 at an address near to where the patient had a job. Based on the proximity of the patient work location and the accident location, and time of the event, the patient was likely exposed to hazardous smoke. The patient has had a chronic cough as a symptom. Since the pollution is a causal factor for a chronic cough, the system determines that the hazardous smoke incident is relevant to that patient and provides this relevant information to the doctor for consideration on the diagnosis/treatment of the patient symptom.

In another example, the patient discusses over a tele-doctor system that he has symptoms such as fever and stomach ache. The patient is in remote area. The system determines that there are other elderly people within the patient area that have similar symptoms. The system has this information through the dynamically updated medical repository, e.g., by receiving updates from a news feed plug-in which has an article about recent health events. Through annotation of the article, the system identifies that within the patient area, there are reports of an increased population of insects which are carriers for a disease that can cause symptoms of fever and stomach ache. This information becomes available to the doctor through the medical dashboard interface. The doctor then can prescribe treatment and recommendations to the patient based on the newly discovered information displayed.

In yet another example, the health care professional enters the patient interview data and the PHR data into the medical dashboard. The resulting display prompts the professional showing several missing facts which if supplied would increase the confidence level of one or more of the displayed causal factors. The patient does not have a firm recollection of the missing facts, but does carry a smartphone and a fitness watch which track location and patient health parameters. The data collected by such personal wearable devices and trackers is processed by the system given permission by the patient. By analyzing the data from the wearable devices, the system identifies the missing facts which are relevant to causal factors, and refreshes the display to show greater confidence levels for some of the causal factors. For example, the GPS data from a tracker will establish if the patient has been in a location within a relevant time period which has been associated with the causal factors associated with the symptoms. For example, visiting very humid areas can trigger a cough for the person susceptible to that condition, e.g., allergy to mold.

The present invention has many advantages over the prior art sources. Embodiments of the invention provide a cloud based solution that consolidates data from various data sources including Internet Of Things devices, health related sources such as the CDC, reports from local hospitals, news reports and weather reports. It dynamically retrieves data facts for the relevant causal factors related to the patient's symptoms and treatment selection. Embodiments of the invention apply dynamically monitored fact data to the association link function, linking causal factors to symptoms so that the medical professional can select a treatment based on which of the causal factors has been determined to be most likely the cause of a symptom for a particular patient. The association link function is statistically trained to evaluate how strong is the impact of various factors on each of the relevant symptoms and treatments and concrete patient data. Embodiments of the invention are used in traditional and remote doctor visits.

While a preferred operating environment and use case has been described, the techniques herein may be used in any other operating environment in which it is desired to deploy services.

As has been described, the functionality described above may be implemented as a standalone approach, e.g., one or more software-based functions executed by one or more hardware processors, or it may be available as a managed service (including as a web service via a SOAP/XML or RESTful interface). The particular hardware and software implementation details described herein are merely for illustrative purposes are not meant to limit the scope of the described subject matter.

More generally, computing devices within the context of the disclosed subject matter are each a data processing system comprising hardware and software, and these entities communicate with one another over a network, such as the Internet, an intranet, an extranet, a private network, or any other communications medium or link. The applications on the data processing system provide native support for Web and other known services and protocols including, without limitation, support for HTTP, FTP, SMTP, SOAP, XML, WSDL, UDDI, and WSFL, among others. Information regarding SOAP, WSDL, UDDI and WSFL is available from the World Wide Web Consortium (W3C), which is responsible for developing and maintaining these standards; further information regarding HTTP, FTP, SMTP and XML is available from Internet Engineering Task Force (IETF).

In addition to the cloud-based environment, the techniques described herein may be implemented in or in conjunction with various server-side architectures including simple n-tier architectures, web portals, federated systems, and the like.

Still more generally, the subject matter described herein can take the form of an entirely hardware embodiment, an entirely software embodiment or an embodiment containing both hardware and software elements. In a preferred embodiment, the module functions are implemented in software, which includes but is not limited to firmware, resident software, microcode, and the like. Furthermore, the interfaces and functionality can take the form of a computer program product accessible from a computer-usable or computer-readable medium providing program code for use by or in connection with a computer or any instruction execution system. For the purposes of this description, a computer-usable or computer readable medium can be any apparatus that can contain or store the program for use by or in connection with the instruction execution system, apparatus, or device. The medium can be an electronic, magnetic, optical, electromagnetic, infrared, or a semiconductor system (or apparatus or device). Examples of a computer-readable medium include a semiconductor or solid state memory, magnetic tape, a removable computer diskette, a random access memory (RAM), a read-only memory (ROM), a rigid magnetic disk and an optical disk. Current examples of optical disks include compact disk-read only memory (CD-ROM), compact disk-read/write (CD-R/W) and DVD. The computer-readable medium is a tangible, non-transitory item.

The computer program product may be a product having program instructions (or program code) to implement one or more of the described functions. Those instructions or code may be stored in a computer readable storage medium in a data processing system after being downloaded over a network from a remote data processing system. Or, those instructions or code may be stored in a computer readable storage medium in a server data processing system and adapted to be downloaded over a network to a remote data processing system for use in a computer readable storage medium within the remote system.

In a representative embodiment, the techniques are implemented in a special purpose computing platform, preferably in software executed by one or more processors. The software is maintained in one or more data stores or memories associated with the one or more processors, and the software may be implemented as one or more computer programs. Collectively, this special-purpose hardware and software comprises the functionality described above.

In the preferred embodiment, the functionality provided herein is implemented as an adjunct or extension to an existing cloud compute deployment management solution.

While the above describes a particular order of operations performed by certain embodiments of the invention, it should be understood that such order is exemplary, as alternative embodiments may perform the operations in a different order, combine certain operations, overlap certain operations, or the like. References in the specification to a given embodiment indicate that the embodiment described may include a particular feature, structure, or characteristic, but every embodiment may not necessarily include the particular feature, structure, or characteristic.

Finally, while given components of the system have been described separately, one of ordinary skill will appreciate that some of the functions may be combined or shared in given instructions, program sequences, code portions, and the like.

Having described our invention, what we now claim is as follows.

The invention claimed is:

1. A method for using a machine learning system to evaluate medical risks comprising:
   by the machine learning system, using a set of symptoms and a set of causal factors, learning using a machine learning process a set of weights in a set of association link formulas, each association link formula for calculating an association link strength between a respective symptom and a respective causal factor, wherein a set of the causal factors include a set of environmental causal factors;
   receiving an input set of symptoms for a first patient;
   retrieving facts about the first patient from a non-medical database;
   by the machine learning system, using the facts about the first patient retrieved from the non-medical database to update the weights in the association link formulas to create an updated set of association link formulas;
   determining which causal factors are relevant to the first patient according to association link strengths in the updated set of association link formulas between respective ones of the relevant causal factors and the input set of symptoms; and
   sending the determined set of relevant causal factors for presentation to a user;
   wherein the association link strengths in the updated set of association link formulas are a function of a weighted set of attributes of the first patient.

2. The method as recited in claim 1, further comprising:
   dynamically monitoring facts from a plurality of data sources;
   storing a set of the dynamically monitored facts in a medical knowledge base; and
   retrieving relevant ones of the stored set of dynamically monitored facts and using the relevant facts to determine the association link strengths for determining which causal factors are relevant to the input symptoms of the first patient.

3. The method as recited in claim 1, wherein
   the machine learning system is a supervised machine learning system selected from the group consisting of a support vector machine, a neural network and a decision tree machine learning system.

4. The method as recited in claim 1, further comprising:
   providing a medical repository knowledge database for storing fact data used to determine association link strengths between respective causal factors and respective symptoms and textual evidence which substantiate the association link strengths between respective causal factors and respective symptoms;
   updating the medical repository knowledge database with new fact data derived from new textual evidence;
   storing the new textual evidence in the medical repository knowledge database; and
   updating the medical repository knowledge database with new fact data gathered from a plurality of plug-ins to external data sources, wherein the non-medical database is coupled to the machine learning system by a respective plug-in.

5. The method as recited in claim 3, wherein a set of the causal factors are internal causal factors, wherein an internal causal factor is an individual characteristic which predisposes an individual to a disease.

6. The method as recited in claim 1, wherein the association link formulas are weighted formulas where weights of relevant facts are learned by the machine learning system, wherein the relevant facts are ones of a set of dynamically monitored facts used to determine the association link strengths for determining which causal factors are relevant to the input symptoms of the first patient.

7. The method as recited in claim 6, further comprising updating a respective association link formula automatically by the machine learning system when a predetermined amount of new information relevant to a corresponding causal factor reaches a threshold.

8. The method as recited in claim 6, wherein the learning of the association link formula evaluates a plurality of candidate algorithms to determine which is the "best fit" given the available data relevant to a corresponding causal factor.

9. The method as recited in claim 1, wherein the environmental causal factors are selected from the group consisting of weather, exposure to pollution, exposure to pathogens, exposure to radiation, and socioeconomic status factors.

10. Apparatus, comprising:
    a processor;
    computer memory holding computer program instructions executed by the processor for performing database maintenance, the computer program instructions comprising:
      machine learning program code, operative to use a set of symptoms and a set of causal factors to learn using a machine learning process a set of weights in a set of association link formulas, each association link formula for calculating an association link strength between a respective symptom and a respective causal factor, wherein a set of the causal factors include a set of environmental causal factors;
      program code, operative to receive an input set of symptoms for a first patient; program code, operative to retrieve facts about the first patient from a non-medical database; machine learning program code to use the facts about the first patient retrieved from the non-medical database to update the weights in the association link formulas to create an updated set of association link formulas;
      program code, operative to determine which causal factors are relevant to the first patient according to association link strengths in the updated set of association link formulas between respective ones of the relevant causal factors and the input set of symptoms; and program code, operative to send the determined set of relevant causal factors for presentation to a user;
      wherein the association link strengths in the updated set of association link formulas are a function of a weighted set of attributes of the first patient.

11. The apparatus as recited in claim 10, further comprising:
    program code, operative to dynamically monitor facts from a plurality of data sources;
    program code, operative to store a set of the dynamically monitored facts in a medical knowledge base; and
    program code, operative to retrieve relevant ones of the stored set of dynamically monitored facts and using the relevant facts to determine the association link strengths for determining which causal factors are relevant to the input symptoms of the first patient.

12. The apparatus as recited in claim 10, wherein the machine learning system is a supervised machine learning system selected from the group consisting of a support vector machine, a neural network and a decision tree machine learning system.

13. The apparatus as recited in claim 11, wherein an identical input set of symptoms is received for the first patient and a second patient, a first set and a second set of relevant facts are respectively retrieved for the first and second patients which results in a first set and a second set of association links being respectively calculated for the first and second patients and a first set and a second set of relevant causal factors being respectively determined for the first and second patients, wherein the first and second set of relevant causal factors are different.

14. The apparatus as recited in claim 12, further comprising:
   symptom annotator program code, operative to identify and extract symptom specific information found in structured or unstructured medical records; and
   causal factor annotator program code, operative to identify and extract causal factor specific information found in structured or unstructured medical records.

15. The apparatus as recited in claim 12, further comprising:
   a set of plug-ins operative to receive new fact data from respective ones of a plurality of external data sources; and
   a set of specialized annotators for annotating data from a respective plug-in of the set of plug-ins.

16. A computer program product in a non-transitory computer readable medium for use in a data processing system, the computer program product holding computer program instructions executed by the data processing system for evaluating medical risks, the computer program instructions comprising:
   machine learning program code, operative to use a set of symptoms and a set of causal factors to learn using a machine learning process a set of weights in a set of association link formulas, each association link formula for calculating an association link strength between a respective symptom and a respective causal factor, wherein a set of the causal factors include a set of environmental causal factors;
   program code, operative to receive an input set of symptoms for a first patient;
   program code, operative to retrieve facts about the first patient from a non-medical database;
   machine learning program code to use the facts about the first patient retrieved from the non-medical database to update the weights in the association link formulas to create an updated set of association link formulas;
   program code, operative to determine which causal factors are relevant to the first patient according to association link strengths in the updated set of association link formulas between respective ones of the relevant causal factors and the input set of symptoms; and
   program code, operative to send the determined set of relevant causal factors for presentation to a user;
   wherein the association link strengths in the updated set of association link formulas are a function of a weighted set of attributes of the first patient.

17. The computer program product as recited in claim 16, further comprising:
   program code, operative to dynamically monitor facts from a plurality of data sources;
   program code, operative to store a set of the dynamically monitored facts in a medical knowledge base; and
   program code, operative to retrieve relevant ones of the stored set of dynamically monitored facts and using the relevant facts to determine the association link strengths for determining which causal factors are relevant to the input symptoms of the first patient.

18. The computer program product as recited in claim 16, wherein the machine learning system is a supervised machine learning system selected from the group consisting of a support vector machine, a neural network and a decision tree machine learning system.

19. The computer program product as recited in claim 16, further comprising:
   a medical repository knowledge database for storing fact data used to determine association link strengths between respective causal factors and respective symptoms, association link strengths between respective diseases and respective symptoms, association link strengths between respective diseases and respective treatments and textual evidence which substantiate the association link strengths.

20. The computer program product as recited in claim 16, further comprising a symptom annotator, a causal factor annotator, a disease annotator and a treatment annotator for respectively annotating and extracting symptom data, causal factor data, disease data and treatment data from structured or unstructured medical records.

21. The computer program product as recited in claim 16, further comprising:
   a set of plug-ins operative to receive new fact data from respective ones of a plurality of external data sources; and
   program code, operative to initiate queries to the set of plug-ins for new fact data responsive to an event, wherein the event is selected from the group consisting of adding a new patient, adding a new doctor, adding a new medical institution and expanding a service area.

* * * * *